US00PP16296P2

(12) United States Plant Patent
Smith

(10) Patent No.: US PP16,296 P2
(45) Date of Patent: Feb. 28, 2006

(54) ***CHRYSANTHEMUM* PLANT NAMED 'SOFT YOCHERYL'**

(50) Latin Name: *Chrysanthemum×morifolium*
Varietal Denomination: Soft Yocheryl

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 129 days.

(21) Appl. No.: 10/937,855

(22) Filed: Sep. 8, 2004

(51) Int. Cl.
*A01H 5/00* (2006.01)

(52) U.S. Cl. ..... Plt./291

(58) Field of Classification Search ..... Plt./291
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Soft Yocheryl', characterized by its upright, outwardly spreading and rounded plant habit; freely branching habit; freely flowering habit; decorative-type inflorescences with elongated oblong-shaped ray florets; light lavender-colored ray florets; natural season flowering in early October in the Northern Hemisphere; and good garden performance.

2 Drawing Sheets

Botanical classification/cultivar designation: *Chrysanthemum×morifolium* cultivar Soft Yocheryl.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Soft Yocheryl'.

The new *Chrysanthemum* is a naturally-occurring whole plant mutation of a proprietary *Chrysanthemum×morifolium* selection identified as code number 93-L603D10, not patented. The new *Chrysanthemum* was discovered and selected by the Inventor as a single flowering plant within a population of plants of the proprietary selection in a controlled environment in Alva, Fla. in November, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Soft Yocheryl has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Soft Yocheryl'. These characteristics in combination distinguish 'Soft Yocheryl' as a new and distinct cultivar of *Chrysanthemum:*

1. Upright, outwardly spreading and rounded plant habit.
2. Freely branching habit.
3. Freely flowering habit.

4. Decorative-type inflorescences with elongated oblong-shaped ray florets.
5. Light lavender-colored ray florets.
6. Natural season flowering in early October in the Northern Hemisphere.
7. Good garden performance.

In side-by-side comparisons conducted in Alva, Fla. under natural season conditions, plants of the new *Chrysanthemum* differed from plants of the parent, the selection identified as code number 93-L603D10, primarily in ray floret coloration as plants of the parent selection had orange-colored ray florets.

Plants of the new *Chrysanthemum* can be compared to plants of the *Chrysanthemum* cultivar Lynn, disclosed in U.S. Plant Pat. No. 8,171. In side-by-side comparisons conducted in Alva, Fla. under natural season conditions, plants of the new *Chrysanthemum* differed from plants of the cultivar Lynn in the following characteristics:

1. Plants of the new *Chrysanthemum* were taller and more upright than plants of the cultivar Lynn.
2. Plants of the new *Chrysanthemum* and the cultivar Lynn differed in ray floret coloration as plants of the cultivar Lynn had slightly darker lavender-colored ray florets.
3. Plants of the new *Chrysanthemum* flowered about five days later than plants of the cultivar Lynn.

Plants of the new *Chrysanthemum* can also be compared to plants of the *Chrysanthemum* cultivar Molfetta, not patented. In side-by-side comparisons conducted in Alva, Fla. under natural season conditions, plants of the new *Chrysanthemum* differed from plants of the cultivar Molfetta in the following characteristics:

1. Plants of the new *Chrysanthemum* were more mounded than plants of the cultivar Molfetta.
2. Plants of the new *Chrysanthemum* flowered about two weeks later than plants of the cultivar Molfetta.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering plant of 'Soft Yocheryl' grown in a container.

The photograph on the second sheet comprises a close-up view of typical inflorescences of the cultivar 'Soft Yocheryl'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Soft Yocheryl.

Commercial classification: Decorative-type garden *Chrysanthemum.*

Parentage: Naturally-occurring whole plant mutation of a proprietary *Chrysanthemum×morifolium* selection identified as code number 93-L603D10, not patented.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum.* Inverted triangle with rounded crown. Stems initially upright, then outwardly spreading. Freely branching with lateral branches potentially developing at every node. Moderately vigorous to vigorous.

*Plant height.*—About 19.5 cm.

*Plant diameter.*—About 28 cm.

*Lateral branches.*—Length: About 20 cm. Diameter: About 7.5 mm. Internode length: About 1.4 cm. Strength: Strong. Texture: Pubescent. Color: Close to 144A.

*Foliage description.*—Leaf arrangement: Alternate. Length: About 4.5 cm. Width: About 3 cm. Apex: Mucronate. Base: Mostly truncate. Margin: Palmately and deeply lobed; sinuses mostly divergent. Texture, upper and lower surfaces: Pubescent. Color: Developing foliage, upper surface: More green than 147A. Developing foliage, lower surface: More green than 147B. Fully expanded foliage, upper surface: Darker green than 147A. Fully expanded foliage, lower surface: Close to 147B. Venation, upper surface: Close to 147A. Venation, lower surface: Close to 147B. Petiole: Length: About 8.5 mm. Diameter: About 3 mm. Texture, upper and lower surfaces: Pubescent. Color, upper surface: Close to 146A. Color, lower surface: Close to 146B to 146C.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about 35 inflorescences develop per plant. Inflorescences persistent. Inflorescences not fragrant.

*Flowering response.*—Under natural season conditions, plants flower in early October in the Northern Hemisphere.

*Inflorescence bud* (*before showing color*).—Height: About 5 mm. Diameter: About 6 mm. Shape: Oblate. Color (lower surface of phyllaries): Close to 146A.

*Inflorescence size.*—Diameter: About 4.75 cm. Depth (height): About 2.1 cm. Disc diameter: Disc florets not observed. Receptacle diameter: About 5 mm. Receptacle height: About 6 mm.

*Ray florets.*—Shape: Elongated oblong. Length: About 2.4 cm. Corolla tube length: About 3 mm. Width: About 7.5 mm. Apex: Acute to emarginate. Margin: Fused. Texture: Smooth, glabrous; satiny. Surface: Initially concave, with development, convex. Orientation: Initially upright, then perpendicular to the peduncle to reflexed. Number of ray florets per inflorescence: About 96 in numerous whorls. Color: When opening, upper and lower surfaces: Close to 155D faintly overlain with close to 77A. Fully opened, upper surface: Close to 155D faintly overlain with close to 77A. Fully opened, lower surface: Close to 155D.

*Phyllaries.*—Quantity per inflorescence: About 20. Length: About 5 mm. Width: About 3.5 mm. Shape: Deltoid, elongated. Apex: Acute. Base: Truncate, fused. Margin: Entire. Texture, upper surface: Smooth, waxy. Texture, lower surface: Pubescent. Color, upper surface: Close to 144A. Color, lower surface: Close to 146A.

*Peduncle.*—Length: First peduncle: About 7 cm. Fourth peduncle: About 9.8 cm. Seventh peduncle: About 13.25 cm. Diameter: About 1.5 mm. Strength: Strong. Aspect: About 45° from vertical. Texture: Pubescent. Color: Close to 144A.

*Reproductive organs.*—Androecium: None observed. Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed.

1. A new and distinct cultivar of *Chrysanthemum* plant named 'Soft Yocheryl', as illustrated and described.

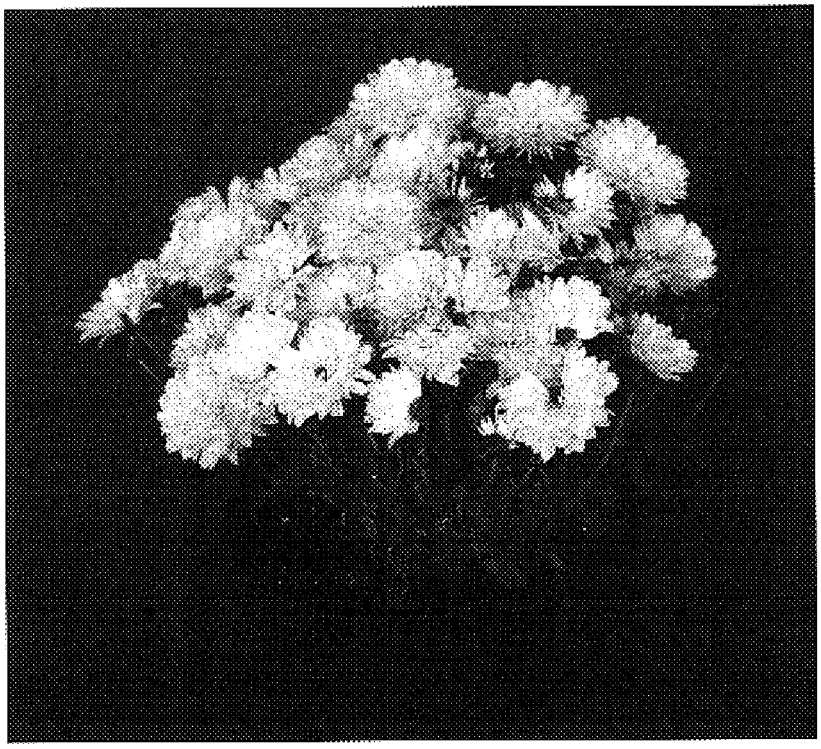

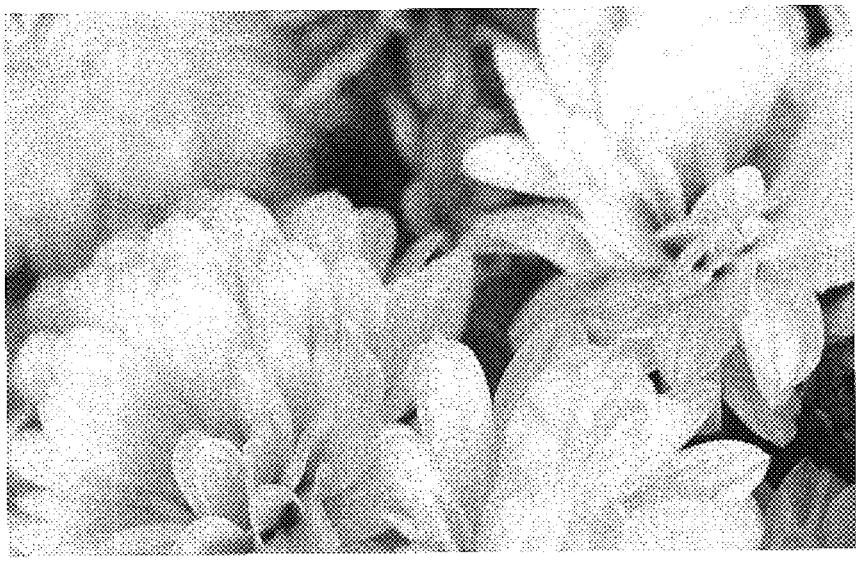

* * * * *